(12) United States Patent
Pugh et al.

(10) Patent No.: US 8,323,464 B2
(45) Date of Patent: *Dec. 4, 2012

(54) METHOD AND APPARATUS FOR ELECTROCHEMICAL ANALYSIS

(75) Inventors: Jerry T. Pugh, Santa Rosa, CA (US); Alastair Hodges, Blackburn South (AU); Garry Chambers, Vermont (AU)

(73) Assignee: Universal Biosensors Pty Ltd, Rowville, Victoria (AU)

( * ) Notice: Subject to any disclaimer, the term of this patent is extended or adjusted under 35 U.S.C. 154(b) by 790 days.

This patent is subject to a terminal disclaimer.

(21) Appl. No.: 11/138,080

(22) Filed: May 25, 2005

(65) Prior Publication Data

US 2006/0266644 A1    Nov. 30, 2006

(51) Int. Cl.
*G01N 27/327* (2006.01)

(52) U.S. Cl. ...................................... 204/400

(58) Field of Classification Search ..... 204/400–403.15; 205/777.5, 778, 792; 422/50–99; 600/345–348
See application file for complete search history.

(56) References Cited

U.S. PATENT DOCUMENTS

| | | | |
|---|---|---|---|
| 4,088,448 A | 5/1978 | Lilja et al. | |
| 4,426,451 A | 1/1984 | Columbus | |
| 4,554,064 A | 11/1985 | McClintock et al. | |
| 4,927,502 A | 5/1990 | Reading et al. | |
| 5,108,564 A | 4/1992 | Szuminsky et al. | |
| 5,120,420 A | 6/1992 | Nankai et al. | |
| 5,171,689 A | 12/1992 | Kawaguri et al. | |
| 5,312,590 A | 5/1994 | Gunasingham | |
| 5,395,504 A | 3/1995 | Saurer et al. | |
| 5,399,256 A | 3/1995 | Bohs et al. | |
| 5,437,999 A * | 8/1995 | Diebold et al. | 204/403.11 |
| 5,525,297 A | 6/1996 | Dinger et al. | |
| 5,609,823 A | 3/1997 | Harttig et al. | |
| 5,679,311 A | 10/1997 | Harttig et al. | |
| 5,741,634 A * | 4/1998 | Nozoe et al. | 204/403.03 |
| 5,797,693 A | 8/1998 | Jaeger | |
| 5,904,898 A | 5/1999 | Markart | |
| 5,942,102 A | 8/1999 | Hodges et al. | |
| 6,027,689 A | 2/2000 | Markart | |
| 6,180,063 B1 | 1/2001 | Markart | |
| 6,193,873 B1 | 2/2001 | Ohara et al. | |
| 6,251,260 B1 | 6/2001 | Heller et al. | |
| 6,284,125 B1 | 9/2001 | Hodges et al. | |

(Continued)

FOREIGN PATENT DOCUMENTS

AU    54873/94    8/1994

(Continued)

OTHER PUBLICATIONS

European Search Report No. EP 03 00 7604 dated May 19, 2003.

(Continued)

*Primary Examiner* — Alex Noguerola
*Assistant Examiner* — Gurpreet Kaur
(74) *Attorney, Agent, or Firm* — Davis Wright Tremaine LLP

(57) ABSTRACT

Electrochemical sensors for investigating a physiological sample and methods of manufacture are disclosed. The sensor includes a longitudinally extending reaction cell, having electrodes and a reagent, and laterally spaced electrical contact points for electrically communication with a meter. An array of such sensors is further disclosed including connective flaps for joining adjacent sensors. In use, the array of sensors can be stored in a folded configuration and dispensed individually.

22 Claims, 10 Drawing Sheets

U.S. PATENT DOCUMENTS

| | | |
|---|---|---|
| 6,299,757 B1 | 10/2001 | Feldman et al. |
| 6,379,513 B1 | 4/2002 | Chambers et al. |
| 6,413,410 B1 | 7/2002 | Hodges et al. |
| 6,447,657 B1 * | 9/2002 | Bhullar et al. ........... 204/403.01 |
| 6,461,496 B1 | 10/2002 | Feldman et al. |
| 6,475,372 B1 | 11/2002 | Ohara et al. |
| 6,676,995 B2 | 1/2004 | Dick et al. |
| 6,689,411 B2 | 2/2004 | Dick et al. |
| 6,716,577 B1 | 4/2004 | Yu et al. |
| 6,749,887 B1 | 6/2004 | Dick et al. |
| 6,780,645 B2 | 8/2004 | Hayter et al. |
| 6,830,934 B1 | 12/2004 | Harding et al. |
| 6,969,450 B2 | 11/2005 | Taniike et al. |
| 2002/0053523 A1 * | 5/2002 | Liamos et al. ................ 205/787 |
| 2002/0084184 A1 * | 7/2002 | Chambers et al. ............ 204/400 |
| 2002/0150501 A1 | 10/2002 | Robertson et al. |
| 2003/0150724 A1 | 8/2003 | Kawanaka et al. |
| 2003/0180814 A1 | 9/2003 | Hodges et al. |
| 2004/0040866 A1 | 3/2004 | Miyashita et al. |
| 2004/0050717 A1 | 3/2004 | Teodorczyk et al. |
| 2004/0203137 A1 | 10/2004 | Hodges |
| 2005/0013731 A1 * | 1/2005 | Burke et al. .................... 422/56 |
| 2006/0134713 A1 | 6/2006 | Rylatt et al. |
| 2010/0006452 A1 | 1/2010 | Hodges et al. |

FOREIGN PATENT DOCUMENTS

| | | |
|---|---|---|
| DE | 3103484 | 8/1982 |
| DE | 3708031 | 11/1987 |
| EP | 0290770 | 11/1988 |
| EP | 0400918 | 12/1990 |
| EP | 0-735363 | 10/1996 |
| EP | 0-609760 | 7/1998 |
| EP | 0-928967 | 3/2004 |
| EP | 1-081490 | 9/2004 |
| JP | 04343065 A | 11/1992 |
| JP | 05002007 | 1/1993 |
| JP | 6-222874 | 8/1994 |
| JP | 3167464 | 3/2001 |
| SU | 1351627 | 3/1986 |
| WO | WO-94/19684 | 9/1994 |
| WO | WO 94/29731 | 12/1994 |
| WO | WO 99/32881 | 7/1999 |
| WO | WO-99/60391 | 11/1999 |
| WO | WO-02/26129 | 4/2002 |

OTHER PUBLICATIONS

Osamu, Niwa, et al. "Electrochemical Behavior of Reversible Redox Species at Interdigitated Array Electrodes with Different Geometries: Consideration of Redox Cycling and Collection Efficiency", Analytical Chemistry; Mar. 1990, vol. 62, No. 5, pp. 447-452.

USPTO, "Office Action," corresponding to related U.S. Appl. No. 11/284,136, mailed on Feb. 11, 2009, 19 pages.

USPTO, "Office Action," corresponding to related U.S. Appl. No. 11/284,136, mailed on Nov. 17, 2009, 19 pages.

USPTO, "Office Action," corresponding to related U.S. Appl. No. 11/284,136, mailed on Aug. 4, 2010, 21 pages.

United States Patent and Trademark Office, "Final Office Action," issued in corresponding U.S. Appl. No. 11/284,136, mailed on Apr. 12, 2011, 28 pages.

United States Patent and Trademark Office (USPTO), Notice of Allowance, issued in corresponding U.S. Appl. No. 11/284,136, mailed Feb. 3, 2012, 8 pages.

* cited by examiner

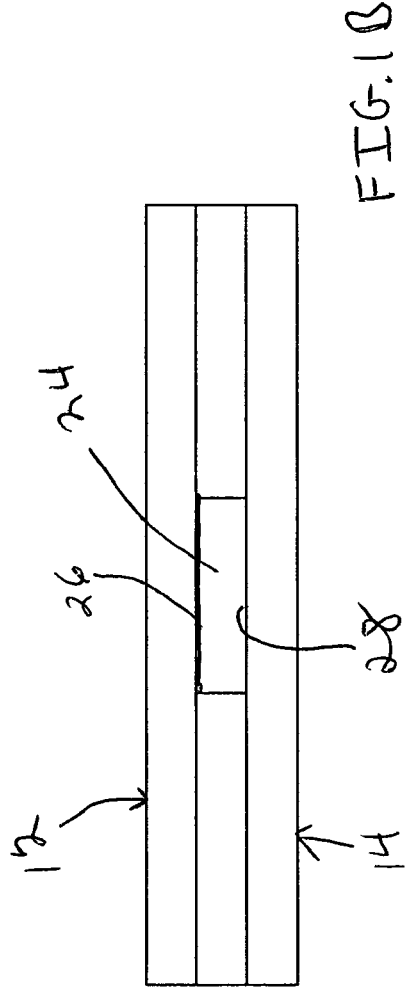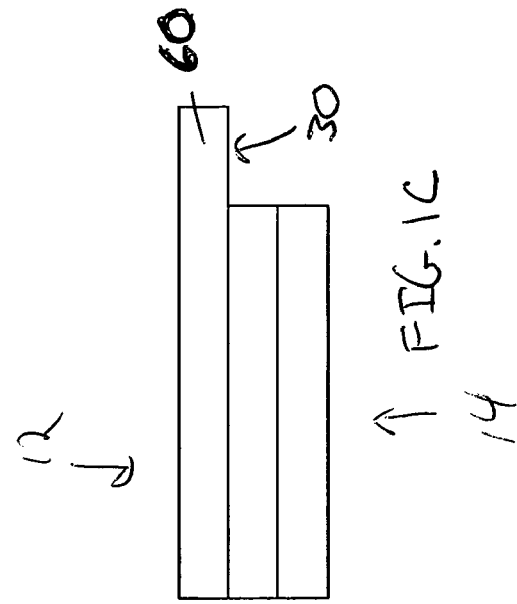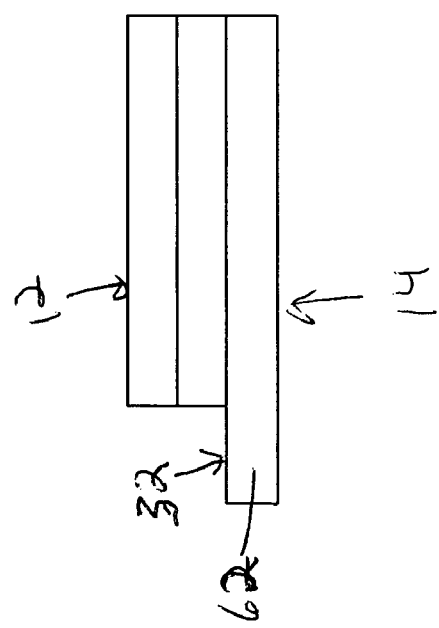

Contact first ribbon  Capillary first ribbon

METHOD AND APPARATUS FOR ELECTROCHEMICAL ANALYSIS

BACKGROUND OF THE INVENTION

Analyte detection in physiological fluids, e.g. blood or blood-derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include glucose for diabetes management, cholesterol, and the like. In response to this growing importance of analyte detection, a variety of analyte detection protocols and devices for both clinical and home use have been developed.

One type of system that allows people to conveniently monitor their blood glucose levels includes a sensor (e.g., a disposable test strip), for receiving a blood sample from a user, and a meter that delivers an electrical impulse to the test strip and collects data during an electrochemical reaction to determine the glucose level in the blood sample. The test strip typically includes an electrical contact area at one end for electrically communicating with the meter and a sample chamber at the other end that contains reagents (e.g., glucose oxidase and a mediator) and electrodes. To begin the test, one end of the test strip is inserted into the meter and the user applies a blood sample to the sample chamber at the other end of the test strip. The meter then applies a voltage to the electrodes to cause a redox reaction and the meter measures the resulting current and calculates the glucose level based on the current. After the test, the test strip can be disposed.

It should be emphasized that frequent measurements of blood glucose levels may be critical to the long-term health of many users. As a result, there is a need for blood glucose measuring systems that are easy to use. However, as sample sizes become smaller, the dimensions of the sample chamber and electrodes in the test strip also become smaller. This, in turn, may make test strips become more difficult to handle.

One solution has been the use of cassettes that hold a series of test strips (e.g., a dozen) that can be mechanically fed into a meter without handling by a user. For example, one such cassette has a circular configuration with axially positioned test strips. Through a complicated mechanized procedure, the cassette is rotated into position and a test strip is fed into the meter. Unfortunately, such systems can require complex mechanical structures that result in added expense and unwanted bulk.

Accordingly, there is a need to provide blood glucose measuring systems and methods with features for measuring blood glucose levels conveniently and reliably, and in particular, a need for test strips that can facilitate such testing.

SUMMARY OF THE INVENTION

Disclosed herein, are electrochemical systems and devices suited for use in the determination of a wide variety of analytes in a wide variety of samples, and are particularly suited for use in the determination of analytes in whole blood or derivatives thereof, where an analyte of particular interest is glucose. As described, the system can comprise individual sensors electrically connectable to a meter, the sensors having a reaction chamber for receiving a sample and spaced apart electrodes for performing an electrochemical analysis. The sensors can be adapted for mating with the meter during analysis such that the meter can send and receive electrical signals to/from the electrodes during analysis.

The individual sensors can include a longitudinally extending reaction chamber for receiving a sample and laterally positioned electrical contact areas for mating with a meter. For example, in one embodiment, a sensor includes a first electrically conductive layer including a first electrode area, an opposing second electrically conductive layer including a second electrode area, and an insulating spacer layer positioned therebetween. The reaction cell is defined by a longitudinally extending opening in the spacer layer and the first and second electrically conductive layers. Spaced laterally from the longitudinal reaction cells, are first and second electrical contact areas.

In one aspect, the reaction cell extends from a proximal end of the spacer layer to a distal end of the spacer layer. For example, the reaction cell can extend the full length of the sensor from a proximal sample ingress port in a proximal sidewall to a distal vent in a distal sidewall. The reaction cell can further be positioned along a central longitudinal axis of the sensor.

Spaced laterally from the longitudinal reaction cell are electrical contact areas which allow the sensor to electrically communicate with a meter. In one aspect, the first electrical contact area is positioned on the first electrically conductive layer and the second electrical contact area is positioned on the second electrically conductive layer. The electrical contact areas can also be positioned on the distal portion of the sensor such that they are spaced from the proximal end of the sensor and/or the reaction cell.

In another aspect, the sensor includes at least one connective flap for mating with an adjacent sensor in an array of sensors. In one exemplary embodiment, the connective flap is a portion of a connective link that mates adjacent sensors and is formed by a portion of the spacer layer that extends beyond the first and second electrically conductive layers. The sensor can include connective flaps positioned at the proximal end for mating with a proximally positioned sensor and at the distal end for mating with a distally positioned sensor.

Further described herein is an array of sensors held together by connective flaps. In one aspect, the flaps are flexible such that individual sensors can pivot with respect to one another. In another aspect, connective flaps allows for storage of the array in a folded configuration. In use, the subject sensors can be positioned within a sensor dispenser in a folded configuration and individually dispensed for use in determining an analyte concentration value in a physiological sample.

For example, the array of sensors can include at least a first and second sensor, each sensor including a first electrically conductive layer, a second electrically conductive layer, and a spacer layer positioned therebetween, the spacer layer including a longitudinal reaction cell. First and second electrical contact areas, positioned on each sensor, are laterally spaced from the longitudinal reaction cell. Connective flaps extend beyond the first and second conductive layers of the first and second sensors to connect the sensors.

Yet further described herein is a method of manufacturing the sensors and sensor arrays. In a first step, a first conductive layer, a second conductive layer and a spacer layer are provided and each layer is cut to form a desired pattern. In one aspect, the patterning step includes forming extension portions in the first and second conductive layers that will define electrical contact areas when the sensor is assembled. In addition, a portion of the first and second conductive layers can be cut away so that a portion of the spacer layer is exposed in the finished sensor. The exposed portions of the spacer layer can form the connective flaps. The patterning step can also include forming longitudinal apertures in the spacer layer that will define the reaction cell in the finished sensor.

A reagent can then be applied to one of the conductive layers and the layers can be combined to form a laminate. Individual sensors are then defined by singulating the laminate. In one aspect, the singulation step includes cutting through the combined layers to separate individual sensor from each other with the exception of the connective flaps. The connective flaps (e.g., a portion of the spacer layer) can remain after the singulation step to flexibly join adjacent sensors.

BRIEF DESCRIPTION OF THE DRAWINGS

FIG. 1B is a cross sectional view of the sensor of FIG. 1A along the line B-B;

FIG. 1C is a cross sectional view of the sensor of FIG. 1A along the line C-C;

DETAILED DESCRIPTION OF ILLUSTRATIVE EMBODIMENTS OF THE INVENTION

Figure 1A:
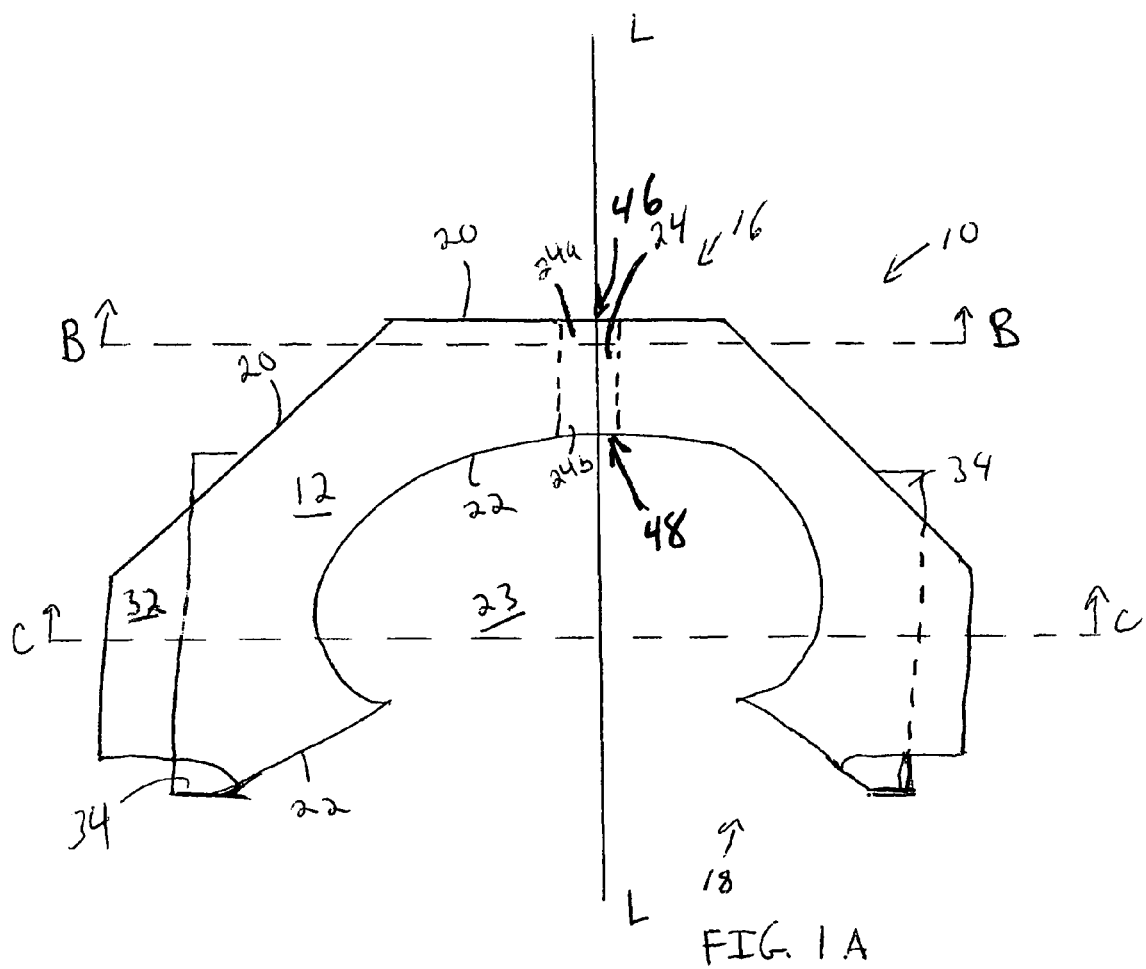
FIG. 1A shows a top view of one embodiment of the sensor described herein.

Described herein are sensors that can include a longitudinally extending reaction chamber for receiving a sample and laterally positioned electrical contact areas for mating with a meter. Further described herein is an array of such sensors, the array including a link between individual sensors that allows for storage of the array in a folded configuration. In use, the subject sensors can be positioned within a sensor dispenser and individually dispensed for use in determining an analyte concentration value in a physiological sample. Yet further described herein is a method of manufacturing the sensors and sensor arrays.

In a first embodiment illustrated FIGS. 1A through 1D, a sensor 10 has a generally planar configuration comprising a top surface 12, a bottom surface 14, and a longitudinal axis L extending between a proximal end 16 and a distal end 18. The sensor further includes a proximal sidewall 20 and a distal sidewall 22. The thickness of sensor 10 can vary across its length and/or width, and as shown in the sectional side views of FIGS. 1B and 1C, sensor 10 can comprise multiple layers laminated together.

Positioned between top and bottom surfaces 12, 14, sensor 10 includes an electrochemical reaction cell 24, having electrodes 26, 28 (FIG. 1B) positioned therein, for electrochemically analyzing a sample. In one aspect, reaction cell 24 extends in the longitudinal direction to define an elongate reaction cell. For example, in FIG. 1A reaction cell 24 is positioned along longitudinal axis L and extends between proximal end 24a and distal end 24b. In one embodiment, the reaction cell runs the length of sensor 10 from proximal sidewall 20 to distal sidewall 22. Alternatively, reaction cell 24 can extend longitudinally along a portion of the sensor such that the reaction cell is shorter than the full length of the sensor.

Physiological fluid can be delivered to reaction cell 24 through a sample ingress port 46. In one aspect, the proximal sidewall 20 of sensor 10 includes sample ingress port 46 for delivery of a sample into reaction cell 24. For example, the proximal end 24a of reaction cell 24 can be open to the atmosphere. In another aspect, the reaction cell can include a second opening 48 that allows for the entrance of a sample and/or the egress of gas. For example, second opening 48 can act as a vent that allows air within the reaction cell to escape as a sample is delivered through sample ingress port 46. Second opening 48 can be positioned at the distal end 24b of reaction cell 24. In one aspect, second opening 48 is at the distal sidewall 22 of sensor 10 and reaction cell 24 extends the full length of sensor 10 from proximal sidewall 20 to distal sidewall 22.

Figure 2A:
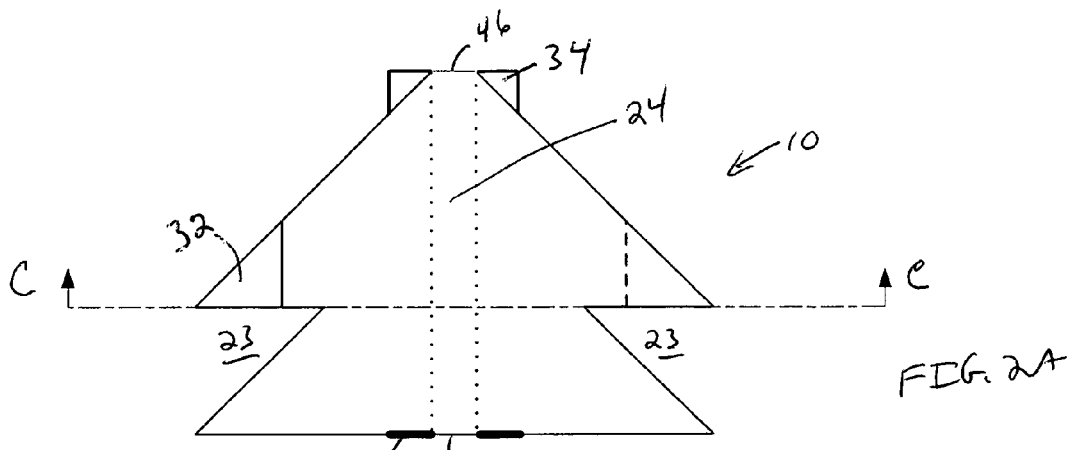
FIG. 2A is a top view of another embodiment of the sensor described herein.
Figure 2B:
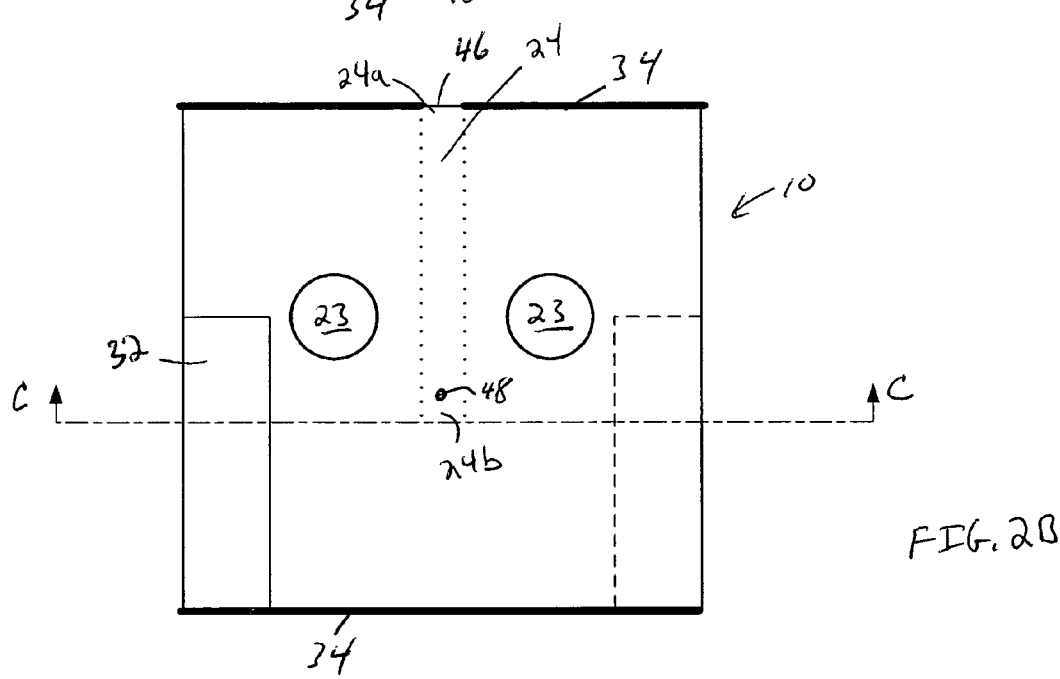
FIG. 2B is a top view of yet another embodiment of the sensor described herein.

In an alternative embodiment, reaction cell 24 extends less than the full length of the sensor and second reaction cell opening 48 is positioned proximally to the distal end 18 of the sensor (FIG. 2B). For example, an opening 48 could be formed through the top or bottom surface of sensor 10.

Spaced laterally from the central longitudinal axis L are a first electrical contact area 30 and a second electrical contact area 32 that allow for electrical communication between a meter (e.g., blood glucose meter) and the reaction cell 24. In use, a meter can mate with sensor 10 such that the contact areas 30, 32 are electrically connected to a circuit within the meter. The first and second electrical contact areas, which are electrically connected to the electrodes 26, 28 within reaction cell 24, allow the circuit to deliver an electric potential to the electrodes.

The first and second electrical contact areas 30, 32, in one aspect, define a portion of the sensor surface that is spaced laterally with respect to the longitudinal axis L of sensor 10. FIG. 1C illustrates a sectional side view of sensor 10 of FIG. 1A along line C-C that shows first and second electrical contact areas 30, 32. The contact areas are positioned adjacent to the outer lateral edges of sensor 10, while the longitudinally reaction cell 24 (FIG. 1B) is positioned along the longitudinal axis. In use, the contact areas can mate with laterally spaced contactors on a meter while the longitudinal reaction cell is available for receiving a sample.

The first and second electrical contact areas are, in one embodiment, positioned on opposite surfaces of sensor 10. For example, the first electrical contact area 30 can be positioned on bottom surface 14 and the second electrical contact area 32 can be positioned on the top surface 12 (FIG. 1C).

To facilitate mating with a meter, the first and second electrical contact area can be positioned distally. For example, contact areas 30, 32 in FIG. 1A are positioned at the distal end of sensor 10. In one embodiment, contact areas 30, 32 are positioned distally with respect to the proximal end 16 of sensor 10, and in another embodiment, the contact areas 30, 32 are positioned distally with respect to reaction cell 24 of sensor 10. As a result, when the sensor 10 is positioned within a meter, the sample ingress port 46 is positioned proximally from the meter while electrical contact areas 30, 32 are positioned distally within the body of meter. In this configuration, a user can easily deliver a sample to sensor 10 while the electrical contact areas are in electrical communication with the meter.

Figure 1D:
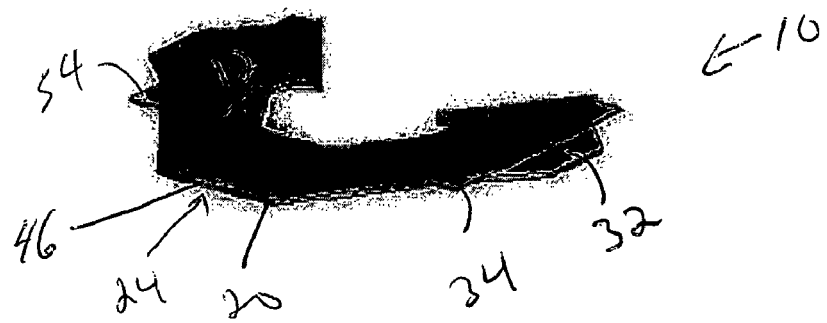
FIG. 1D is a perspective view of the sensor of FIG. 1A.
Figure 1E:
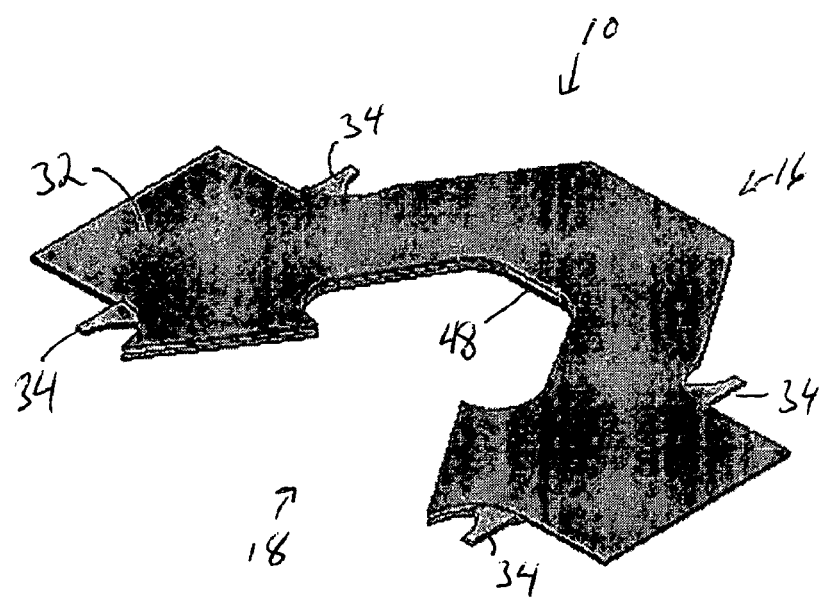
FIG. 1E is a perspective view of another embodiment of the sensor of FIG. 1A.

In one embodiment, electrical contact areas 30, 32 have a tapered proximal end as shown in FIG. 1D. Alternatively, electrical contact areas 30, 32 could have a rectangular configuration as shown in FIG. 1E. One skilled in the art will appreciate that electrical contact areas 30, 32 can have a variety of shapes and sizes that will allow the sensor 10 to electrically communicate with a meter.

Sensor 10 can further include linking features that allow sensor 10 to mate with an adjacent sensor to create an array of sensors. In one embodiment, the linking features include connective flaps 34 that extend from the edge of the sensor. Each connective flap represents one half of a link that can mate two adjacent sensors. Sensor 10 can include multiple flaps 34 to provide multiple links to an adjacent sensor, and in one embodiment sensor 10 includes two pairs of spaced apart flaps. As shown in FIG. 1A, a first pair of flaps extends from the proximal sidewall 20 and a second pair of flaps extends from the distal sidewall 22.

Figure 2C:
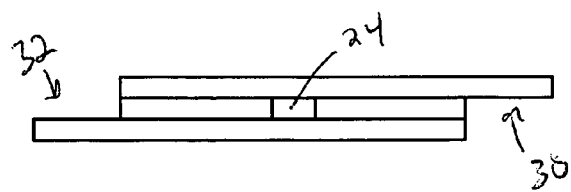
FIG. 2C is a cross sectional view of the sensors illustrated in FIGS. 2A and 2B along the line C-C.

Sensor 10, in one embodiment, has a generally "V" shape as illustrated in FIG. 1A through 1D. Sensor 10 can alternatively have another shape as illustrated in FIGS. 2A through 2C. For example, FIG. 2A illustrates a "tree" configuration including longitudinally extending reaction cell 24, lateral spaced connection areas 30, 32, and connective flaps 34. FIG. 2B illustrates a rectangular configuration including longitudinally extending reaction cell 24, lateral spaced connection areas 30, 32, and a connective flaps 34.

Regardless of the sensor's geometric configuration, sensor 10 can include mating features that facilitate mating sensor 10 with a meter and/or a sensor dispenser. For example, the sensor disclosed in FIG. 1A includes a central opening 23 between the legs of the "V" that can receiving an actuating portion of a sensor dispenser and/or a meter. In one embodiment, opening 23 is positioned between the contact areas 30, 32 as shown in FIG. 1C. The meter and/or sensor dispenser can use opening 23 to hold and/or advance the sensor. Other mating features, such a lateral openings 23 in the sides of the sensor illustrated in FIG. 2A, or apertures 23 extending through the sensor illustrated in FIG. 2B can alternatively be used to mate with a sensor dispenser and/or a meter.

Figure 3:
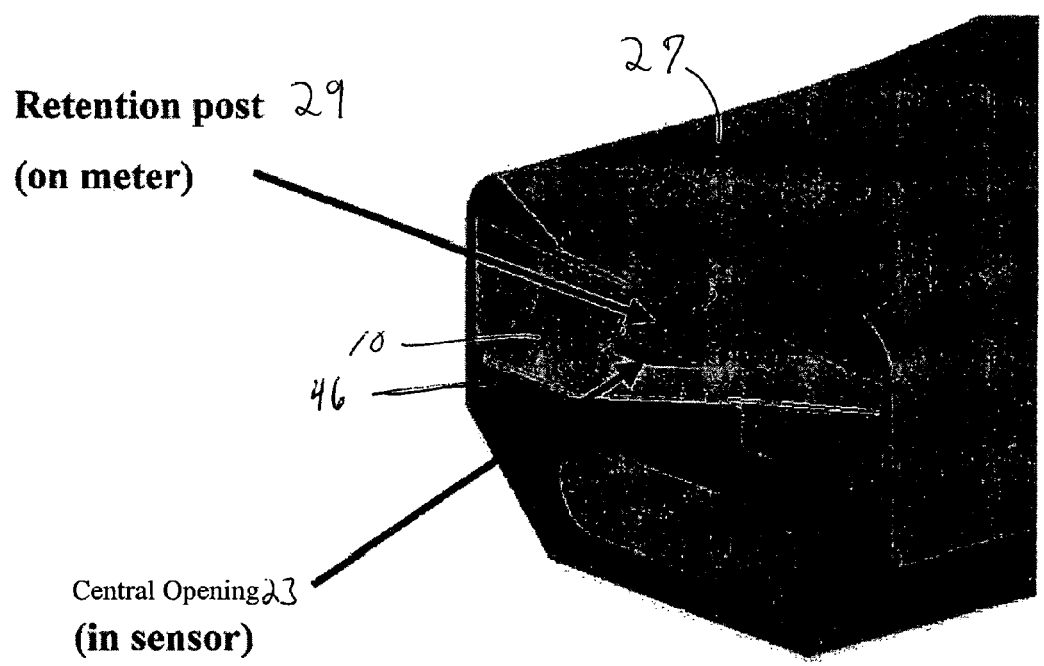
FIG. 3 is a perspective view of one embodiment of the sensor described herein positioned within a meter.

FIG. 3 illustrates the sensor of FIG. 1A positioned within a meter 27. As shown, a retention post 29 can mate with central opening 23 to hold sensor 10 within meter 27. One skilled in the art will appreciate that sensor 10 can mate with a meter and/or sensor dispenser via a variety of opening and/or surface features.

Figure 4:
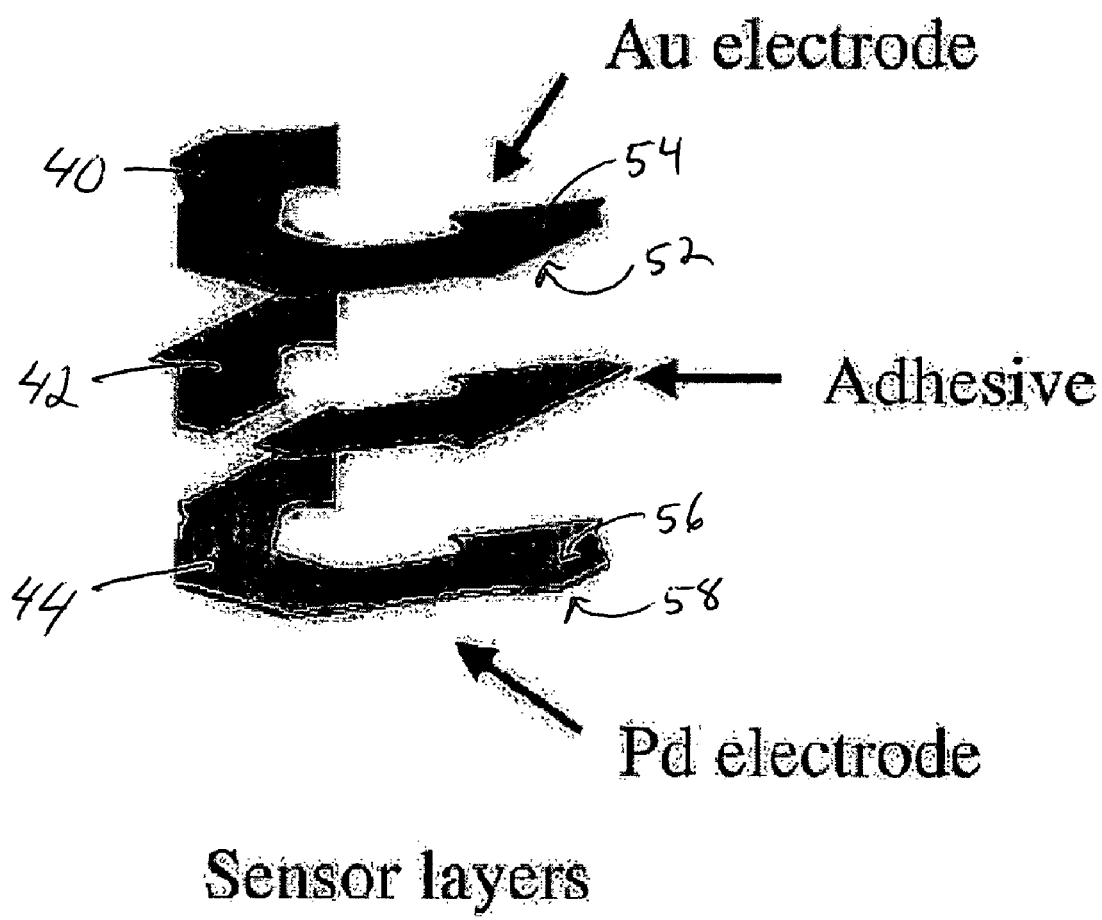
FIG. 4 is an exploded view of one embodiment of the sensor described herein.

Sensor 10, in one embodiment, comprises a multi-layer laminate including a first electrically conductive layer 40, a spacer layer 42, and a second electrically conductive layer 44 as shown in FIG. 4. The electrically conductive layers can comprise an electrically conductive material and optionally an insulating substrate. Spacer layer 42, positioned between the electrically conductive layers, can comprise an insulating material, and in one aspect, binds the layers of the laminate together. One skilled in the art will appreciate that the spacer layer 42, first electrically conductive layer 40, and/or second electrically conductive layer 44 can comprise more than a single layer (e.g., the layers could comprise multiple layers of insulation, adhesives, etc.).

The first and second electrically conductive layers can provide the conductive surface required for the first and second electrodes 26, 28 and the contact areas 30, 32. In one aspect, first electrode 26 and first contact 30 are positioned on the first electrically conductive layer 40, and the second electrode 28 and second contact area 32 are positioned on the second electrically conductive layer 44. The first and second electrically conductive layers can further provide an electrically conductive track between the first and second electrodes 26, 28 and the first and second contact areas 30, 32, respectively, to electrically connect the electrodes to the electrical contact areas 30, 32.

In one embodiment, first and/or second electrically conductive layers may be a conductive material such as gold, palladium, carbon, silver, platinum, iridium, doped tin oxide, and stainless steel. In addition, the electrically conductive layers can be formed by disposing a conductive material onto an insulating sheet (not shown) by a sputtering or a screen-printing process. In one exemplary embodiment, one electrically conductive material may be sputtered gold and the other conductive material can be sputtered palladium. Suitable materials that may be employed as the insulating sheet on which the electrically conductive material is deposited include plastic (e.g. PET, PETG, polyimide, polycarbonate, and/or polystyrene), silicon, ceramic, glass, and combinations thereof.

Spacer layer 42 can comprise a variety of insulting (non-electrically conductive or minimally electrically conductive) materials. Exemplary spacer materials can include, for example, plastics (e.g. PET, PETG, polyimide, polycarbonate, and/or polystyrene), silicon, ceramic, glass, and combinations thereof. Spacer layer 42 can also include, or be formed substantially of, an adhesive.

An opening in spacer layer 42 provides an area for reaction cell 24. In one aspect, a longitudinal aperture 66 in spacer layer 42 defines the sidewalls of the reaction cell. The opposed first and second electrically conductive layers, positioned on either side of spacer layer 42, can define the top and bottom walls of reaction cell 24. The area of first electrically conductive layer 40 exposed within reaction cell 24 can define the first electrode 26 and the area of the second electrically conductive layer 44 exposed within reaction cell 24 can define second electrode 28. In one aspect, the first and second electrodes are in a non-planer configuration, and preferably, are in an opposed configuration.

A reagent layer 72 can be disposed within reaction cell 24 using a process such as, for example, slot coating, coating by dispensing liquid from the end of a tube, ink jetting, and screen printing. Such processes are described, for example, in the following U.S. Pat. Nos. 6,749,887; 6,689,411; 6,676,995; and 6,830,934, which are hereby incorporated by reference in their entirety. In one embodiment, reagent layer 72 is deposited onto the first electrode and includes at least a mediator and/or an enzyme. A mediator can be in either of two redox states which can be referred to as an oxidizable substance or a reducible substance. Examples of suitable mediators include ferricyanide, ferrocene, ferrocene derivatives, osmium bipyridyl complexes, and quinone derivatives. Examples of suitable enzymes include glucose oxidase, glucose dehydrogenase (GDH) based on a pyrroloquinoline quinone co-factor, and GDH based on a nicotinamide adenine dinucleotide co-factor. One exemplary reagent formulation, which would be suitable for making reagent layer 72, is described in pending U.S. application Ser. No. 10/242,951 which is hereby incorporated by reference in its entirety.

A sample (e.g., whole blood) can be delivered to reaction cell 24 in spacer layer 42 via sample ingress port 46. In one aspect, sample ingress port 46 is formed by longitudinal aperture 66 in spacer layer 42 that extends to the proximal sidewall of sensor 10. For example, the proximal end 24a of reaction cell 24 can be open to the atmosphere. The second opening 48 can similarly be formed by extending longitudinal aperture 66 to the distal sidewall of sensor 10, and in one embodiment, second opening 48 is at the distal end 18 of sensor 10 and aperture 66 extends the full length of sensor 10 from proximal sidewall 20 to distal sidewall 22.

In an alternative embodiment, reaction cell 24 extends less than the full length of the sensor and second reaction cell opening 48 is positioned proximally to the distal end 18 of the sensor (FIG. 2B). Instead of aperture 66 extending to distal sidewall 22, the second opening 48 could be formed through first and/or second electrically conductive layer 40, 44.

In one embodiment, sensor 10 is adapted to draw a sample into reaction cell 24 via capillary action. For example, the height of the reaction cell can be sized such that when a liquid sample is brought into contact with sample ingress port 46, capillary action draws the sample into reaction cell 24. One skilled in the art will appreciate that the dimensions of reaction cell 24, sample ingress port 46, and second opening 48, as well as, the surface properties of reaction cell 24, can be adjusted to provide the desired capillary effect.

Figure 5A:
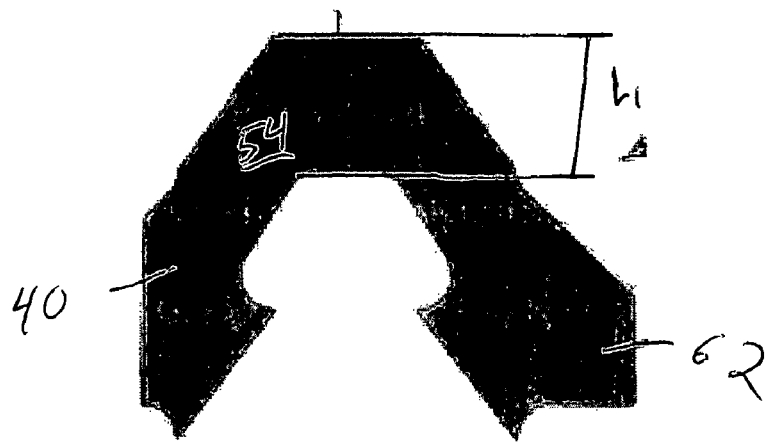
FIG. 5A is a top view of a first electrically conductive layer of one embodiment of the sensor described herein.
Figure 5B:
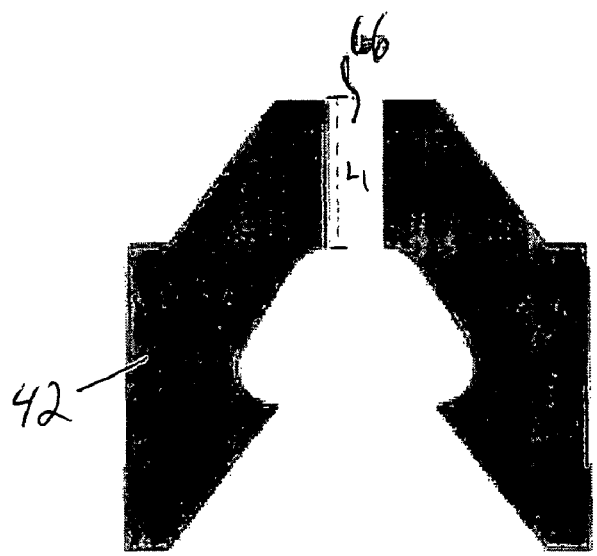
FIG. 5B is a top view of a spacer layer of one embodiment of the sensor described herein.
Figure 5C:
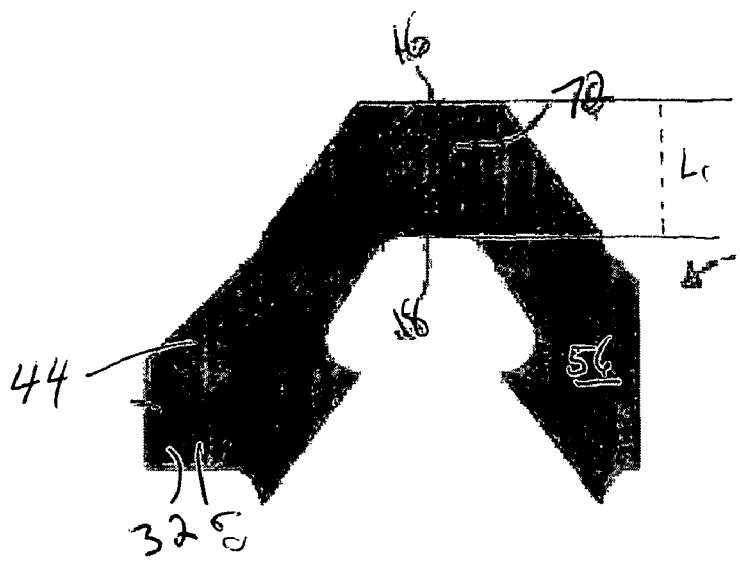
FIG. 5C is a top view of a second electrically conductive layer of one embodiment of the sensor described herein.

Layers 40, 42, and 44 are individually illustrated in FIGS. 5A through 5C, respectively. In one aspect, the electrically conductive layers include an electrically conductive material on one surface and an insulating material on the opposite surface. For example, first electrically conductive layer 40 can include an electrically conductive material on a bottom surface 52 and an insulating material on a top surface 54, while the second electrically conductive layer 44 includes an electrically conductive material on a top surface 56 and an insulating material on a bottom surface 58. When the layers are combined into a laminate, the electrically conductive material on bottom surface 52 faces the electrically conductive material on top surface 56.

The first and second electrically conductive layers 40, 44 can be shaped such that when combined, sensor 10 includes laterally spaced electrical contact areas 30, 32. As shown in FIGS. 5A and 5C, the first and second electrically conductive layers include extension portions 60, 62. When combined, the extension portion 62 of the first electrically conductive layer 40 can extend beyond the spacer layer 42 and the second electrically conductive layer 44 to form second electrical contact area 30. Similarly, extension portion 60 of the second electrically conductive layer 44 can extend beyond the spacer layer 42 and the first electrically conductive layer 40 to form first electrical contact area 32.

In one embodiment, extension portions 60, 62 are positioned toward the distal end 18 of the first and second electrically conductive layers such that the first and second electrical contact areas 30, 32 are located distally with respect to the reaction cell 24 formed by aperture 66. As a result, when the sensor 10 is positioned within a meter, the sample ingress port 46 extends proximally from the meter while the electrical contact areas are positioned within the body of the meter.

Spacer layer 42, as illustrated in FIG. 5B, can include longitudinal aperture 66 that will form reaction cell 24 when the layers are combined. In one embodiment, length $L_1$ of aperture 66 (e.g., along the longitudinal axis) is equal to the length $L_1$ of first and second electrically conductive layers 40, 44, such that the proximal end of aperture 66 forms sample ingress port 46 and the distal end of aperture 66 forms the second opening 48. In an alternative embodiment, the length of aperture 66 could extend less than the full length of spacer layer 42 (not shown) to provide a reaction cell 24 that extends less than the full width of sensor 10.

Spacer layer 42 can also provide the connection between adjacent sensors, and in one embodiment, spacer layer 42 is shaped such that when layers 40, 42, and 44 are brought together, an area of spacer layer 42 extends beyond the first and second electrically conductive layers 40, 44. For example, connective flaps 34 can be formed by a portion (or portions) of spacer layer 42 extending beyond the first and second electrically conductive layers. The connective flaps 34 can join with connective flaps on an adjacent sensor to provide a connection between sensors. When the connective flaps of adjacent sensor are joined, the connected sensors form an array of two or more sensors. As shown in FIG. 1A, sensor 10 can include a pair of proximal flaps 34 and a pair of distal flaps 34. The proximal set of connective flaps can be connected to a set of distal connective flaps on an proximally positioned adjacent sensor and the distal set of connective flaps can be connected to a set of proximal connective flaps on a distally positioned adjacent sensor. While a set of two connective flaps are shown in the FIGS., in an alternative embodiment, more flaps (e.g., three or more) or fewer flaps (one) could form the connection between adjacent sensors in an array of sensors.

In one aspect, connective flaps 34 allow adjacent sensors to move relative to one another by creating a pivot point (e.g., hinge) such that adjacent sensors can pivot with respect to one another. In order to provide relative movement between sensors, spacer layer 42 can be formed from a flexible or bendable material. For example, flaps (and spacer layer 42) can be formed from a polymeric material such as a polyester film. One such material is Melinex® PET polyester film from Dupont, Inc. One skilled in the art will appreciate that the spacer material and spacer layer thickness can be chosen to control the amount of flap flexibility.

In an alternative embodiment, flaps 34 are defined by a portion of a different layer. For example, electrically conductive layers 40 and 44 could include a portion that defines a connective flap. Alternatively, sensor 10 could include an additional layer, positioned for example, outside electrically conductive layers 40, 44, that forms connective flaps 34.

Connective flaps 34 preferably have enough strength to hold sensors 10 together, but can be broken or torn to allow individual sensors to be dispensed. One skilled in the art will appreciate that the cross sectional area of the flaps (i.e., thickness and/or width) and/or flap material can be adjusted to provide the desired flap strength. In addition, the flaps can be notched or perforated to facilitate tearing.

Figures 6A, 6B:
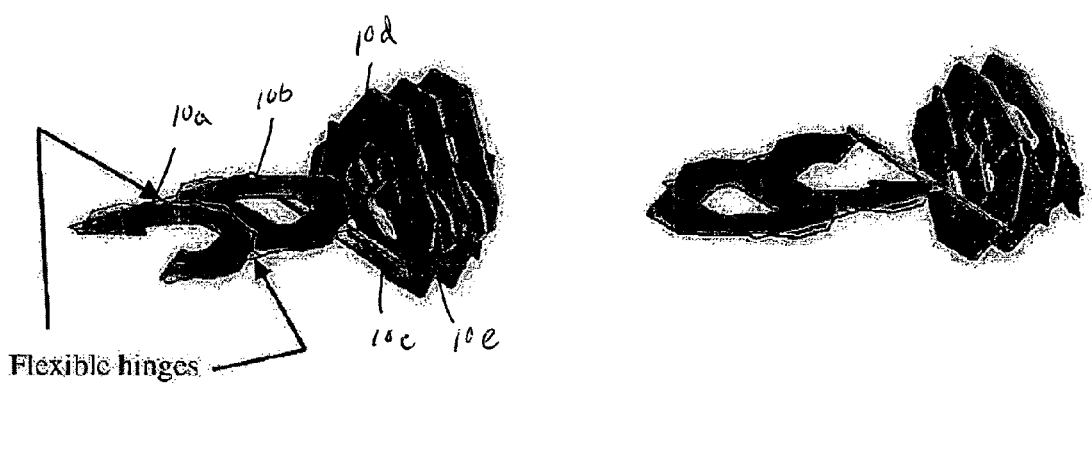
FIG. 6A is a perspective view of an array of sensors positioned for delivery in a contact area first orientation.
FIG. 6B is a perspective view of an array of sensors positioned for delivery in a reaction cell first orientation.

FIGS. 6A and 6B illustrate an array or a series of connected sensors which are mated to one another via connective flaps 34. Sensors 10a and 10b can be positioned in a coplanar configuration and then pivoted into a folded configuration as shown between sensors 10c, 10d, and 10e. The folded configuration allows the sensors to be stored using a minimal amount of space. When needed, the sensors can then be unfolded and individually dispensed. FIG. 6A illustrates a configuration in which individual sensors are dispensed distal-end-first and FIG. 6B illustrates a configuration in which the sensors are dispensed in proximal-end-first.

Figure 7A:
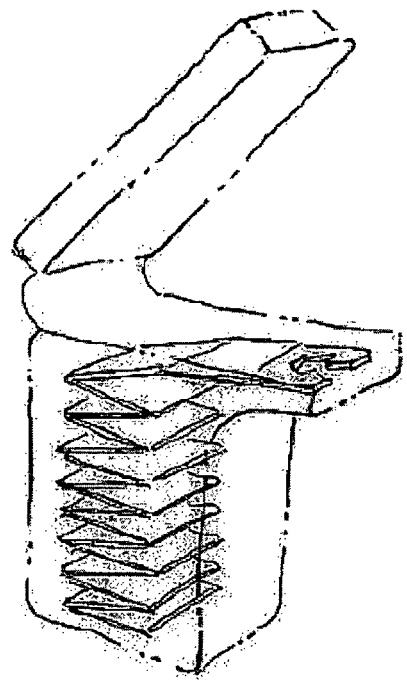
FIG. 7A is a schematic of an array of sensors positioned within a sensor dispenser.
Figure 7B:
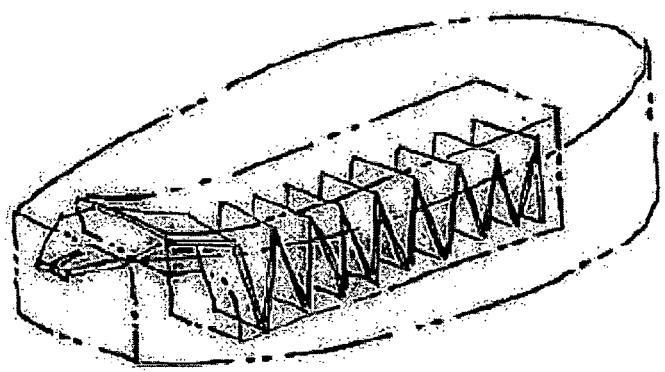
FIG. 7B is a schematic of an array of sensors positioned within a meter.

In use, an array of sensors can be dispensed from a stand alone sensor dispenser 50, such as shown in FIG. 7A, or positioned within a meter 52 as shown in FIG. 7B. Sensor dispensers that can be used with the sensor 10 are disclosed, for example, in a U.S. Application entitled "Sensor Dispenser Device and Method of Use," filed contemporaneously, and hereby incorporated by reference in its entirety.

Figure 8:
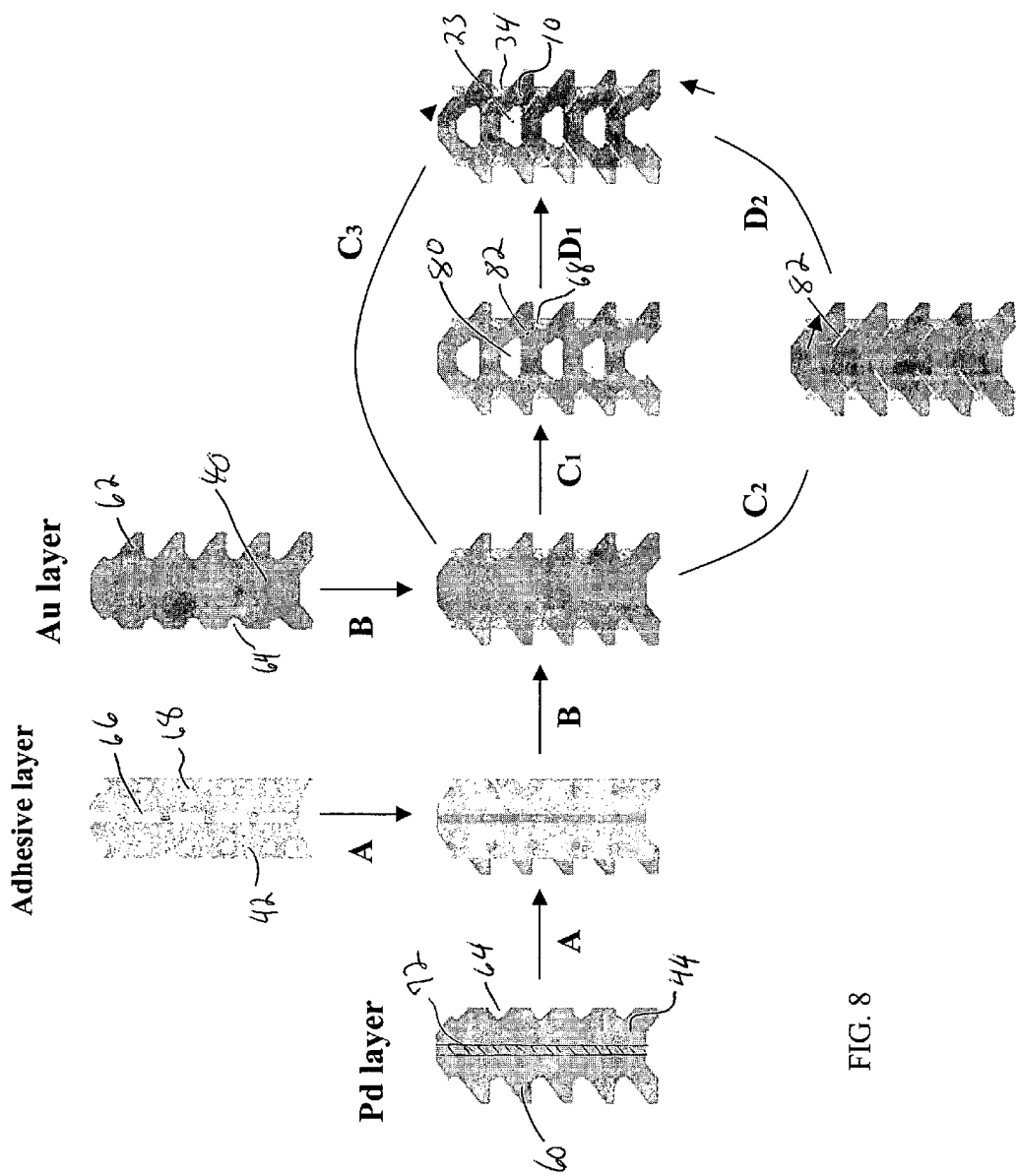
FIG. 8 is a flow chart of exemplary manufacturing process steps that can used to produce the sensor of FIG. 1A.

In one embodiment, sensors 10 are manufactured in an array, such that the produced sensors are connected to one another. In use, an individual sensor can be removed (e.g., torn off) and dispensed for individual use. FIG. 8 illustrates one embodiment of the method for manufacturing an array of sensors 10. In a first step, continuous lengths of electrically conductive layer material and spacer layer material are provide and cut in a desired pattern. For example, in a cutting step, a portion of material is cut away to pattern first and second electrically conductive layers 40, 44 and spacer layer 42. One skilled in the art will appreciate that sensor 10 can have a variety of shapes, and the pattern of the layers will depend on the desired configuration of sensor 10. While the method of manufacturing is illustrated with respect to the sensor illustrated in FIG. 1A, sensors having a shape, such as those illustrated in FIGS. 1E, 2A, and 2B, can be similarly produced.

After the cutting step, layers 40, 42, 44 preferably have a shape such that the resulting sensor 10 will have first and second laterally spaced electrical contact areas 30, 32. For example, the patterned first and second electrically conductive layers 40, 44 can include extension portions 62, 60, that define electrical contact areas 30, 32.

In addition, an area(s) of the first and second electrically conductive layers can be cut away to expose a portion of spacer layer 42. In one aspect, notches 64 are cut in the lateral edge(s) of the electrically conductive layer to expose a portion of space layer 42 in the finished sensor. The exposed portions of spacer layer 42 can form the connective flaps 34. One skilled in the art will appreciate that connective flaps could alternatively be formed by a portion of spacer layer 42 that has a greater width that the electrically conductive layers.

Spacer layer 42 can also be patterned, and in one aspect, a portion of spacer layer 42 is removed to form longitudinal aperture 66 that will become reaction cell 24. Additional portions of spacer layer 42 can also be removed, such as, for example, apertures 68 can be formed in the spacer layer 42 to facilitate singulation (aperatures 68 can provide connective flaps 34 shaped like those of FIG. 1E).

Prior to combining the layers, reagent 72 (as discussed above) can be added to at least one of the layers. In one embodiment, reagent 72 is positioned along the longitudinal axis of layer 40, such that reagent 72 of layer 40 and aperture 66 of layer 42 will be aligned when the layers are combined.

Once reagent 72 has been applied and the layers 40, 42, 44 of sensor 10 have been cut to the desired pattern, sensor 10 can be assembled. One skilled in the art will appreciate that the order in which the layers are combined can be varied. In one embodiment illustrated in FIG. 8, spacer layer 42 and second electrically conductive layer 44 are combined and then the first electrically conductive layer 40 is adhered to the combined layers.

Once layers 40, 42, 44 have been combined, a central aperture 80 is preferably cut to form opening 23 and the individual sensors are singulated. These steps can be performed contemporaneously, as shown by path $C_3$, or in series as illustrated by paths $C_1D_1$ and $C_2D_2$. For example, central aperture 80 can be created in the combined layers, and then the sensors can be singulated along line 82, or the sensor can be singulated first and then central aperture 80 can be cut. In yet another embodiment, central aperture 80 could be created in each individual layer prior to combining the layers. One skilled in the art will appreciate that these cutting and/or perforating steps can be performed using a variety of cutting tools.

The singulation step includes cutting and/or perforating the combined layers to define individual, connected sensors. In one embodiment, the singulation process leaves only a portion of the spacer layer 42 connecting adjacent sensors. For example, the combined layers can be cut along line 82 which extend from aperture 80 to aperture 68. The remaining, uncut portion of spacer layer 42 holds the adjacent sensors together and allows them to flex or pivot relative to one another. The intact portions of layer 42 can define connective flaps 34.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An electrochemical device, comprising:
a first electrically conductive layer including a first electrode area and an opposing second electrically conductive layer including a second electrode area, the first and second electrically conductive layers being separated by an insulating spacing layer, wherein at least one of the first or second electrically conductive layers comprises an electrically conductive material and an insulating material, wherein the electrically conductive material is coextensive with the insulating material;
a reaction cell defined by the first and second electrically conductive layers, and a longitudinally extending opening in the spacing layer, the reaction cell including a proximal sample ingress port and a distal end, the reaction cell extending from a proximal sidewall of the device to a distal sidewall of the device, the distal end being at the distal sidewall;
the ingress port comprising at least one of the first electrically conductive layer and the second electrically conductive layer, wherein the ingress port is proximal to and in fluid communication with the reaction cell; and
first and second electrical contact areas positioned on opposite lateral sides of the longitudinal reaction cell, the first electrical contact area positioned on the first electrically conductive layer and the second electrical contact area positioned on the opposing second electrically conductive layer.

2. The device of claim 1, wherein the reaction cell includes a distal vent.

3. The device of claim 1, wherein the first and second electrically conductive layers are spaced such that a sample brought into contact with the proximal opening is drawn into the reaction cell via capillary action.

4. The device of claim 1, wherein the reaction cell is positioned along a central longitudinal axis.

5. The device of claim 4, wherein the first electrical contact area is positioned adjacent to a first lateral edge of the device and the second electrical contact area is positioned adjacent to a second lateral edge the device.

6. The device of claim 1, wherein a connective flap extends beyond the first and second electrically conductive layers for connecting with another electrochemical device.

7. The device of claim 1, wherein at least a portion of the spacing layer extends beyond the first and second electrically conductive layers to define a connective flap for connecting an adjacent electrochemical device.

8. The device of claim 7, further comprising two pairs of connective flaps.

9. The device of claim 1, wherein the first electrical contact area is positioned on a top surface of the first electrically conductive layer and the second electrical contact area is positioned on a bottom surface of the second electrically conductive layer.

10. The device of claim 1, wherein the first and second electrical contact areas are spaced longitudinally from the reaction cell.

11. A strip of connected electrochemical sensors, comprising:
at least two sensors;
a first sensor comprising,
(a) a first electrically conductive layer, second electrically conductive layer, and a spacer layer positioned therebetween, the spacer layer including a longitudinal aperture defining a reaction cell, the first sensor comprising a proximal end and a distal end, an ingress port at the proximal end comprising at least one of the first electrically conductive layer and the second electrically conductive layer, wherein the ingress port is in fluid communication with the reaction cell, the reaction cell extending from the proximal end to the distal end of the sensor,
(b) first and second electrical contact areas positioned on opposite lateral sides of the longitudinal reaction cell, and
(c) at least one connective flap at the distal end for connecting with another electrochemical sensor; and
a second sensor connected to the first sensor, comprising,
(a) a first electrically conductive layer, second electrically conductive layer, and a spacer layer positioned therebetween, the spacer layer including a longitudinal aperture defining a reaction cell, the second sensor comprising a proximal end and a distal end, an ingress port at the proximal end comprising at least one of the first electrically conductive layer and the second electrically conductive layer, wherein the ingress port is in fluid communication with the reaction cell, the reaction cell extending from the proximal end to the distal end of the sensor,
(b) first and second electrical contact areas positioned on opposite lateral sides of the longitudinal reaction cell, and
(c) at least one connective flap at the proximal end connected to the at least one connective flap at the distal end of the first sensor,
wherein at least one of the first or second electrically conductive layers comprises an electrically conductive material and an insulating material, wherein the electrically conductive material is coextensive with the insulating material.

12. The sensors of claim 11, wherein the at least one connective flap of the first and second sensors comprises a portion of the spacer layer.

13. The sensors of claim 11, wherein the first and second sensors are adapted to pivot with respect to one another.

14. The sensors of claim 11, wherein the first and second sensors comprise an additional layer, and the additional layer provides the connective flap of the first and second sensor.

15. A method of manufacturing an array of sensors, comprising:
providing a longitudinally extending first electrically conductive layer having a first electrode surface, a longitudinally extending second electrically conductive layer having a second electrode surface, and a longitudinally extending spacer layer having a longitudinal aperture, wherein the spacer layer is continuous along the longitudinal direction,
wherein at least one of the first or second electrically conductive layers comprises an electrically conductive material and an insulating material, wherein the electrically conductive material is coextensive with the insulating material;
applying a reagent to the first electrically conductive layer;
combining the first electrically conductive layer, spacer layer, and second electrically conductive layer, such that the first and second electrode surfaces are opposing, and a portion of the first electrically conductive layer extends laterally beyond the spacer layer and the second electrically conductive layer to define a first electrical contact area, and a portion of the second electrically conductive layer extends laterally beyond the first electrically conductive layer and spacer layer to define a second electrical contact area, and an ingress portion comprises at least one of the first electrically conductive layer and the second electrically conductive layer; and
singulating the combined layers along the lateral direction to define discrete sensors, each of the discrete sensors comprising a proximal end and a distal end, wherein the singulating generates the proximal end and the distal end of the discrete sensors.

16. The method of claim 15, wherein an adhesive on the spacer layer holds the combined layers together.

17. The method of claim 15, wherein the longitudinal apertures in the spacer layer provides a reaction cell in each discrete sensor.

18. The method of claim 15, wherein the singulation step leaves only the spacer layer holding adjacent sensors together.

19. The method of claim 15, including cutting the first and second electrically conductive layers prior to combining the layers.

20. The method of claim 15, further comprising cutting holes through the layers at regular intervals.

21. The method of claim 20, wherein the step of combining the layers occurs before the step of cutting holes through the layers.

22. The method of claim 15, wherein the discrete sensors are held together by connective flaps, wherein the distal end of one sensor are connected to the proximal end of the next sensor by the connective flaps.

* * * * *